United States Patent [19]

Barton et al.

[11] 3,991,103

[45] Nov. 9, 1976

[54] 5H DIBENZO (a,d) CYCLOHEPTENE, 10,11 DIHYDRO, 5(1-HALO-3-DIMETHYLAMINOPROP-1-YLIDENE) DERIVATIVES

[75] Inventors: Derek Harold Richard Barton, London, England; Robert Henry Hesse, Cambridge, Mass.

[73] Assignee: Research Institute for Medicine and Chemistry Inc., Cambridge, Mass.

[22] Filed: Oct. 21, 1974

[21] Appl. No.: 516,735

[30] Foreign Application Priority Data

Oct. 22, 1973 United Kingdom............... 49054/73

[52] U.S. Cl.................. 260/501.1; 260/247.1 R; 260/247.5 R; 260/247.7 N; 260/247.7 T; 260/290 R; 260/290 HL; 260/333; 260/326.5 S; 260/326.5 R; 260/326.5 C; 260/326.5 CA; 260/326.5 E; 260/293.56; 260/293.58; 260/294.8 B; 260/570.5 CA; 260/570.5 P; 260/501.18; 424/248; 424/263; 424/274; 424/330

[51] Int. Cl.².................. C07C 87/00; C07C 87/29

[58] Field of Search................ 260/501.1, 570.5 LA, 260/570.5 P, 501.18

[56] References Cited

UNITED STATES PATENTS 3,372,196   3/1968   Engelhardt...................... 260/501.1
3,445,519   5/1969   Kollonitsch..................... 260/501.1

OTHER PUBLICATIONS

Barton et al., Chemical Communications, pp. 227–228, (1969).

Barton et al., Chemical Communications, pp. 804–808, (1968).

Tatlow et al., Advances in Fluorine Chemistry, Butterworth & Co., p. 183, (1973).

Weininger, Contemporary Organic Chem., Holt Rinehart & Wilson Inc., pp. 179–183 (1972).

Primary Examiner—James O. Thomas, Jr.
Assistant Examiner—G. Breitenstein
Attorney, Agent, or Firm—Bacon & Thomas

[57] ABSTRACT

11-Halo derivatives of amitriptyline and its analogues, i.e. 5-(1'-halo-3'-aminoprop-1'-yl-idene)-5H-dibenzo[a,d]-10,11-dihydrocycloheptenes and corresponding 11-oxa analogues as well as the acid addition salts thereof, have notable anti-depressant and tranquillising activity. They are prepared by reacting a 5-(3'-aminoprop-1'-ylidene)-5H-dibenz[a,d]-10,11-dihydrocycloheptene or an 11-oxa analogue thereof, or an acid addition salt thereof, with an electrophilic halogenating agent.

7 Claims, No Drawings

5H DIBENZO (a,d) CYCLOHEPTENE, 10,11 DIHYDRO, 5(1-HALO-3-DIMETHYLAMINOPROP-1-YLIDENE) DERIVATIVES

This invention relates to novel dibenzocycloheptenes related to amitriptyline which have notable anti-depressant and tranquillising activity.

The new compounds may be generally characterised as 11-halo derivatives of amitriptyline and its analogues and are thus generally 5-(1'-halo-3'-aminoprop-1'-ylidene)-5H-dibenzo [a,d]-10,11-dihydrocycloheptenes and corresponding 11-oxa analogues as well as the acid addition salts thereof.

The compounds according to the present invention may, in general, be represented by the general formula

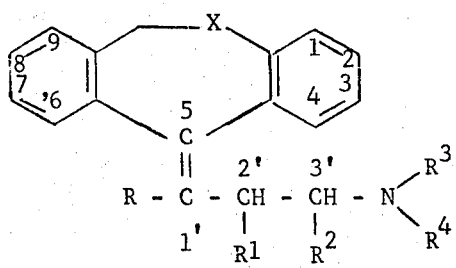

I where R is a halogen atom, e.g. a fluorine, chlorine or bromine atom; X is —CH$_2$— or —O—; R$^1$ and R$^2$ which may be the same or different are hydrogen atoms or alkyl groups; R$^3$ and R$^4$ which may be the same or different represent alkyl groups which may carry substituents such as aryl groups, e.g. phenyl groups, or alkylamino groups, e.g. diethylamino or dimethylamino groups, R$^4$ alternatively representing a hydrogen atom; or R$^3$ and R$^4$ together with the intervening N represent a heterocyclic group; and where the nucleus may optionally carry further substituents such as alkyl, alkoxy, or alkylthio groups or halogen atoms.

R$^3$ and R$^4$ are preferably lower alkyl groups, e.g. with 1–6 carbon atoms, such as methyl, ethyl, propyl, butyl, isopropyl, or hexyl groups, optionally carrying an aryl substituent, as in the benzyl or phenethyl groups, or a dialkylamino group such as a 2-diethylaminoethyl or 2-dimethylaminoethyl group.

R$^3$ and R$^4$ together with the intervening N may represent a heterocyclic group such as a cyclic amine with 5 to 8 ring members, optionally containing further heteroatoms. R$^3$ and R$^4$ may thus, for example, comprise a cyclic monoamine group such as a piperidine, pyrrolidine, hexamethylenimine or morpholine group or a cyclic diamine group such as a piperazine, N-alkylpiperazine or N-hydroxyalkylpiperazine, e.g. an N-methylpiperazine or N-hydroxyethyl piperazine, group.

R$^1$ and R$^2$ preferably represent hydrogen atoms or lower alkyl groups, e.g. with 1–6 carbon atoms, such as methyl groups.

Nuclear substituents which may be present include halogen atoms, especially chlorine atoms; alkyl groups such as methyl groups; alkoxy groups such as methoxy or ethoxy groups or alkylthio groups such as methylthio, ethylthio or isopropylthio groups. Such substituents are preferably in one or more of the 2-, 3-, 7- and 8-positions, for example, 2-chloro, 3-chloro, 7-chloro, 8-chloro, 3,7-dichloro, 2-methoxy or 3-methylthio substituents. The alkyl, alkoxy and alkyl groups preferably contain 1–6 carbon atoms.

The compounds according to the present invention preferably carry a 5-(1-halo-3-dimethylaminoprop-1-ylidene)-side chain.

The acid addition salts of the new bases according to the invention include, for example, salts with mineral acids such as hydrochloric, hydrobromic or sulphuric acid, as well as salts with organic acids such as maleic or tartaric acid.

The compounds exhibit notable anti-depressant and tranquillising activity, and in general show a more rapid onset of activity than amitriptyline.

According to the further feature of the present invention we provide pharmaceutical compositions comprising a compound of the general formula 1 as defined above together with a pharmaceutical carrier or excipient. Suitable forms include the usual types of anti-depressant formulation using especially the oral route, for example, tablets, coated tablets, capsules, syrups and elixirs. The compositions are preferably dosage unit forms, in particular tablets and coated tablets. Each dosage unit preferably contains 2.5 to 300 mg, advantageously 10 to 200 mg of active ingredient.

The compounds of general formula I may, in general, be prepared by electrophilic halogenation of the corresponding 1'-unsubstituted compounds.

According to a further feature of the present invention we provide a process for the preparation of the compounds of the invention in which a 5-(3'-aminoprop-1'-ylidene)5H-dibenz[a,d]10,11-dihydrocycloheptene or an 11-oxa analogue thereof, i.e. a compound of the general formula

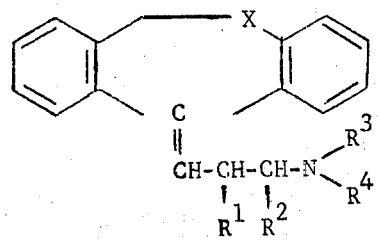

II (where X, R$^1$, R$^2$, R$^3$ and R$^4$ have the above meanings and the nucleus may carry substituents), or an acid addition salt thereof, is reacted with an electrophilic halogenating agent.

For the introduction of a fluorine atom in the 1'-position, the electrophilic halogenating reagent is preferably a hypofluorite reagent, e.g. a perfluoroalkyl hypofluorite such as trifluoromethyl hypofluorite.

For the introduction of the bromine or chlorine, the reagent may be molecular chlorine or bromine or an appropriate halo amide or imide or a halogen complex with an organic base, e.g. a cyclic ether such as dioxan, a tertiary nitrogen base such as pyridine, or a tertiary aliphatic amine. The halogenation and particularly the fluorination reaction, is improved by carrying out the reaction in the presence of an acid which can protonate the 3'-amino function and protect it from the halogenating reagent. Trifluoroacetic acid is particularly useful for this purpose. Such as acid may serve as solvent or another solvent such as a halohydrocarbon, e.g. a chlorohydrocarbon or a fluorocarbon, may be present. The first step in the halogenation is undoubtedly attack of the electrophilic halogen at the 1'-position of the propylidene chain. This leaves a positive charge at the 5-position of the cylcoheptene ring. This charge may be removed by loss of the proton from the 1'-position to give directly the prop-1-ylidene compound of interest or in the event that nucleophilic species are present in the medium one of these may be added at the 5-position. In general, perfluroalkyl hypofluorites give not only perfluoroalkoxy anions but, by disproportionation, fluoride ions. Other nucleophilic species include hydroxyl ions, from any water present, acyloxy ions from acids which may be present, e.g. acetic or trifluoroacetic acid, or chloride and bromide ions from molecular halogen.

In most cases, both processes occur simultaneously and it is necessary to eliminate the 1'-hydrogen along with the substituent at the 5-position in order to maximise yields of the required product. Where the substitutent at the 5-position is a halogen atom or a perfluoroalkyl group (e.g. trifluoromethoxy), this may be eliminated by treatment with a base, e.g. an alkali metal (for example sodium or potassium) alkoxide or hydroxide or an amine e.g. a tertiary amine such as 1,4-diazabicyclooactane. Where the 5-substituent is an acyloxy group such as acetoxyl or trifluoroacetoxyl or is a hydroxyl group, the elimination is best accomplished by treatment with an acid such as hydrogen chloride, hydrogen brominde, hydrogen iodide or sulphuric acid. If 5-substituents of more than one type are present and both acidic and basic elimination are needed, it is preferable to effect the elimination with acid prior to elimination with base, since base treatment of compounds having an acyloxy group in the 5-position gives rise to compounds with a hydroxyl group at the 5-position and treatment of these structures with alkali may result in formation of epoxides and/or rearrangement products.

Acid addition salts of the new bases according to the invention may readily be prepared by addition of an appropriate acid. Conveniently, the base is dissolved in a solvent such as ethanol from which the salt can subsequently be precipitated by addition of a miscible non-solvent therefore such as ether. Salt formation is of assistance in purifying the bases since these are mostly oils at room temperature.

The following examples are given by way of illustration only:

PREPARATION 1

3'-dimethylamiprop-1'-ylidene-5H-dibenzo [a,d] 10,11-dihydro-cycloheptene (Amitriptyline)

Amitriptylene hydrochloride [m.p. 190°–192° C; ultraviolet absorption $\lambda_{max.}$ 240nm ($\epsilon$ 13,800) (CH$_3$OH] was neutralised with a 5% sodium bicarbonate solution. After extracting the aqueous layer three times with chloroform and drying, a quantitative recovery of a pale yellow oil was obtained. The amine was homogeneous by t.l.c. (silicic acid. CH$_3$OH:CH$_3$COOC$_3$H$_5$ 1:1). NMR (CDCl$_3$) spectrum: 2.1 (s, N-methyl): 2.33 (s, methylene): 3.13 (bm, methylene): 5.87 (t, vinyl proton): 7.03 and 7.13 ppm (sm, aromatic protons). IR (film) spectrum: 2950 (s); 2790 (s); 1490 (s); 1460 (s); 1440 (s); 1050 (m-s); 1040 (m-s); 775 (s); 770 (s); 740 (s); and 715 cm$^{-1}$(s).

EXAMPLE 1

1'-Fluoro-amitriptyline

Amitriptyline base (2mM) in 9.4 ml. dried methylene chloride, 1.5 eq. trifluoroacetic acid, and 0.5 eq. trifluoroacetic anhydride were added to a flask and cooled to −78° C. This solution was then added to a −78° C solution of 2mM CF$_3$OF in 50 ml. CF$_2$Cl$_2$ and stirred for 1¼ hrs. The solution changed from bright yellow to colourless. The reaction mixture was concentrated and redissolved in chloroform. After washing with 5% aqueous sodium bicarbonate and water, the organic layer was concentrated to yield an oil (647 mg.).

The presence of the trifluoroacetate adduct (1800 cm$^{-1}$), the trifluoromethoxy adduct (vs, 1200 cm$^{-1}$), and the title compound (1675 cm$^{-1}$) were observed in the IR (Film) spectrum. The NMR (CDCl$_3$) spectrum showed two methyls at 2.27 and 2.15 ppm.

The adduct (475 mg) in 2 ml. absolute ethanol and 1 ml. concentrated hydrochloric acid was refluxed for 2½ hrs. The reaction mixture was cooled, diluted, neutralised (sodium bicarbonate), and extracted with ethyl ether. Concentration yielded the title compound as a yellow-brown oil (372 mg).

IR (CHCl$_3$) spectrum: 1675 (vinyl fluoride).

NMR (CDCl$_3$) spectrum: 2.13 (s, N-methyl); 2.1–3.9 (m, methylene) 7.1–7.4 ppm (aromatic protons).

FMR (CFCl$_3$) spectrum: +107.8 (t, vinyl fluoride) and +56.4–59.6 ppm (sm, trifluoromethoxy) (trace).

EXAMPLE 2

Maleate salt of 1'-fluoro-amitriptyline

1'-Fluoro-amitriptyline (0.83 mM) in 3 ml. absolute ethanol was added to an ethanolic solution of 1 eq. maleic acid and warmed for 5 mins. Evaporation of the solvent gave a crude weight of 340 mg. Crystallisation from ethyl acetate-ethyl ether gave an analytical sample of the title compound (m.p. 117–119° C) with ultraviolet absorption spectrum: $\lambda_{max.}$ 235 nm ($\epsilon$ 16,500). Anal. Cal'd for $C_{24}H_{26}N_1O_4F$: C, 70.07; H, 6.33; F. 4.62; N, 3.41. Found: C, 70.04, H, 603; F, 4.50; N, 3.34[3].

EXAMPLE 3

1'-Bromo-amitriptyline

Amitriptyline base (1 mM) was dissolved in 2 ml. carbon tetrachloride. To this was added a 1:1 mixture of trifluoroacetic acid: acetic acid, and 1 eq. bromoine (5% bromine/carbon tetrachloride stock solution). After stirring for 1¼ hr. at ca. 0° C, the solution had become a light orange. The solution was concentrated and chloroform was added. After washing with aqueous sodium bicarbonate and water, a red-orange oil was obtained.

NMR (CDCl$_3$) spectrum: 2.13 (s, N-methyl); 1.0–3.90 (m, methylene), 7.0–743 ppm (sm, aromatic protons).

IR (CHCl$_3$) spectrum: appearance of two bands (2850 and 2800 [m-s]) and of four bands (1750, 1690, 1635 and 1570 cm$^{-1}$[w]). T.l.c. (silicic acid, CH$_3$OH:CH$_3$CO$_2$C$_2$H$_5$ 1:;) showed three components with the major component slightly less polar than I.

Dehydrobromination was achieved by reacting the initial bromination product (245 mg) with 1,4-diazabicyclooactane (701 mg) in 20 ml. refluxing dioxan for two days. Dilution with water and extraction with chloroform yielded a mixture of products. IR(CHCl$_3$) spectrum showed a very intense 1730 cm$^{-1}$ band. After thick layer chromatography (CH$_3$OH:CH$_3$CO$_2$C$_2$H$_5$ 1:1), the title compound (major component with R$_f$ a. 0.53) was isolated.

NMR (CDCl$_3$) spectrum: 2.13 (s, N-methyl); 2.37–3.77 (sm, methylene); 7.17–7.21 ppm (aromatic protons).

IR (CHCl$_3$) spectrum: 1730 cm$^{-1}$ band was absent.

Ultraviolet absorption spectrum (CH$_3$OH): λ$_{max}$. 240.5 nm (ε 10,142).

EXAMPLE 4

Tartrate salt of 1'-bromo-amitriptyline

1'-Bromo-amitriptyline (0.44 mM) in 8 ml. absolute ethanol was added to an ethanolic solution of 1.5 eq. d-tartaric acid and warmed for 5–10 mins. The title compound was precipitated with ethyl ether as a white crystalline powder. After purity and identification checks, the overall yield from amitripyline base was 30%. M.P. 163.5°–165° C.

The tartrate gave a positive Beilstein test.

Ultraviolet absorption spectrum (CH$_3$OH): λ$_{max}$. 242.7 nm (ε 12,195).

Mass spectrum: 355 and 357 (1:1).

Anal. Calc'd. for C$_{24}$H$_{28}$N$_1$O$_6$Br$_1$: C, 56.92; H, 5.57; N, 2.77. FOUND; C, 56.65; H, 5.63; N, 2.54.

EXAMPLE 5

1'-Chloro-amitriptyline

A solution of chlorine was prepared by bubbling chlorine gas into a cylinder of glacial acetic acid. An aliquot was removed and added to aqueous potassium iodide solution. The molarity of Cl$^-$ was determined with titration with a standard sodium thiosulfate solution.

One equivalent was then added to a solution of 1 mM amitriptyline, 1 eq. trifluoroacetic acid, 1 eq. acetic acid, and 5 ml. carbon tetrachloride. After 1½ hours at ca. 0° C, the solution changed from a yellow-green to colourless.

NMR (CDCl$_3$) spectrum: no vinyl proton at 5.7 ppm.
IR (CHCl$_3$) spectrum: 1800 (s) (trifluoroacetate); 1750 (s) (acetate); and 1680 (s) cm$^{-1}$.

NMR suggested virtually no halogen in the 5-position, no dehydrohalogenation reaction was effected.

Instead, the chlorination product (1 mM) in 3 ml. absolute ethanol was treated with refluxing 0.8 ml. concentrated hydrochloric acid. The mixture was diluted, neutralised (sodium bicarbonate), and extracted with chloroform. IR (CHCl$_3$) spectrum: 1720 cm$^{-1}$. After thick layer chromatography (CH$_3$OH:CH$_3$CO$_2$C$_2$H$_5$), the title compound was isolated as the second band (major component) (196 mg.) NMR (CDCl$_3$) spectrum: 2.08 (s, N-methyl); 2.17–3.53 (m, methylene); 7.12 (sm, aromatic protons).

IR (CHCl$_3$) spectrum: no absorption in 1600–1800 cm$^{-1}$ region.

EXAMPLE 6

Tartrate salt of 1'-Chloro-amitriptyline

1-Chloro-amitriptyline (196 mg) in 3 ml. absolute ethanol was added to an ethanolic solution of 1.1 eq. d-tartaric acid and warmed for 5–10 mins. The title compound was precipitated with ethyl ether as a white powder. After purity and identification checks, the overall yield from amitriptyline base was 32%.

The tartrate (m.p. 158–159° C) had an ultraviolet absorption spectrum (CH$_3$OH): λ$_{max}$. 241.1 nm (ε 11,135).

Mass spectrum:
Anal.: Calc'd for C$_{24}$H$_{28}$N$_1$O$_6$Cl$_1$: C, 62.40; H, 6.11; N, 3,03; Cl, 7.68.

Further physical characteristics of the products of the Examples are given in the following table:

TABLE

| Example | M.Pt. | CH$_3$OH λ$_{Max}$. |
|---|---|---|
| 1 | 190–192[1] | 240 nm (ε 13.800) |
| Amitriptyline hydrochloride | 196–197[2] | |
| 2 | 117–119 | 235 nm (ε 16,500) |
| 4 | 163.5–165 | 242.7 nm (ε 12,195) |
| 6 | 158–159 | 241.1 nm (ε 11,135) |

We claim:
1. A compound having the formula

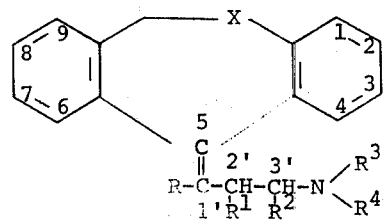

I wherein R is halogen, X is —CH$_2$—, R$^1$ and R$^2$ are selected from the group consisting of hydrogen and lower alkyl, R$^3$ and R$^4$ are each selected from the group consisting of lower alkyl and lower alkyl substituted by phenyl, dimethylamino or diethylamino; or R$^4$ may be hydrogen; and nuclear substituents at the 2, 3, 7 and 8 positions may be the same or different and are selected from the group consisting of hydrogen, halogen, C$_{1-6}$ alkyl, C$_{1-6}$ alkoxy and C$_{1-6}$ alkylthio; and acid addition salts thereof.

2. Compounds according to claim 1 in which R is a fluorine, chlorine or bromine atom.

3. Compounds according to claim 1 which carry a 5-(1-halo-3-dimethyl-aminoprop-1-ylidene)-side chain.

4. The compound of claim 1 wherein the acid addition salt is formed with hydrochloric, hydrobromic, sulphuric, maleic or tartaric acid.

5. 1'-Fluoroamitryptiline and its maleate salt.
6. 1'-Bromoamitryptiline and its tartrate salt.
7. 1'-Chloroamitrypliline and its tartrate salt.

* * * * *